United States Patent [19]

Scholz et al.

[11] Patent Number: 5,225,513
[45] Date of Patent: Jul. 6, 1993

[54] CASTING ARTICLE AND COMPOSITION

[75] Inventors: Matthew T. Scholz, Woodbury; Robert A. Scherrer, White Bear Lake, both of Minn.

[73] Assignee: Minnesota Mining and Manufacturing Company, St. Paul, Minn.

[21] Appl. No.: 742,047

[22] Filed: Aug. 8, 1991

[51] Int. Cl.⁵ ............................................. C08G 18/18
[52] U.S. Cl. ..................................... 528/53; 523/111; 428/260
[58] Field of Search .................... 528/53; 523/111; 128/90; 428/260

[56] References Cited

U.S. PATENT DOCUMENTS

| | | | |
|---|---|---|---|
| 4,011,223 | 3/1977 | Priest et al. | 528/53 |
| 4,012,445 | 3/1977 | Priest et al. | 528/53 |
| 4,376,438 | 3/1983 | Straube et al. | 128/90 |
| 4,411,262 | 10/1983 | von Bonin et al. | 128/90 |
| 4,433,680 | 2/1984 | Yoon | 128/90 |
| 4,502,479 | 3/1985 | Garwood et al. | 128/90 |
| 4,667,661 | 5/1987 | Scholz et al. | 128/90 |
| 4,705,840 | 11/1987 | Buckanin | 528/53 |

OTHER PUBLICATIONS

West German Pat. No. DE 1,933,411 abstracted at Chem. Abs. 76:153583m 1971.
Soviet Union Pat. No. 278027 abstracted at Chem. Abs. 74:53512c 1970.
Khim.-Farm.Zh. 1967, 1, 26 abstracted at Chem. Abs. 67:82022d.
Khim.-Far.Zh. 1973, 7, 10 abstracted at Chem. Abs. 91:123691n.
Acta. Pol. Pharm. 1980, 37, 397 abstracted at Chem. Abs. 95:80069d.
Pol. J. Pharmacol. Pharm. 1978, 30, 497 abstracted at Chem. Abs. 91:32648n.
Farm. Az. 1990, 1, 38 abstracted at Chem. Abs. 114:42025q.
Khim.-Farm. Az. 1983, 17, 916 abstracted at Chem. Abs. 99.169415u.

*Primary Examiner*—John Kight, III
*Assistant Examiner*—Rachel Johnson
*Attorney, Agent, or Firm*—Gary L. Griswold; Walter N. Kirn; F. Andrew Ubel

[57] ABSTRACT

Catalyzes methods and curable compositions involving amino-ester catalysts and isocyanate-functional materials. Also disclosed are casting articles and methods of orthopedic casting.

9 Claims, No Drawings

CASTING ARTICLE AND COMPOSITION

FIELD OF THE INVENTION

This invention relates to catalysts for curing isocyanate-functional materials. In another aspect, this invention relates to curable compositions comprising an isocyanate-functional material and a catalyst. This invention also relates to casting articles and methods of orthopedic casting.

BACKGROUND OF THE INVENTION

Orthopedic casts for use in treating bone fractures or other conditions requiring immobilization of a body member are generally formed from a sheet of fabric or scrim material coated or impregnated with a substance that hardens into a rigid structure after the sheet has been wrapped around the body member.

Many orthopedic casts now commonly used are comprised of a backing impregnated with a water-curable isocyanate-functional prepolymer. The backing can be knitted, woven, or nonwoven scrim comprised of natural, polymeric, or glass fibers. The preferred scrim materials are knitted fiberglass scrims. These casts when cured have a higher strength to weight ratio than plaster-of-paris, are more resistant to water and provide good radiolucency.

U.S. Pat. No. 4,411,262 (von Bonin), U.S. Pat. No. 4,502,479 (Garwood), and U.S. Pat. No. 4,667,661 (Scholz et al.) disclose water-curable isocyanate-functional prepolymers useful in orthopedic bandages. The prepolymer typically includes a tertiary amine catalyst in an amount selected to optimize the "set" time. After the resin-impregnated scrim has been immersed in water, sufficient "working time", e.g., 3 to 5 minutes, should be provided in which the wrapping is accomplished and the cast is manually molded into a desired shape. However, after the cast is shaped, the resin should continue to harden and rapidly build strength, typically in 15-30 minutes, into a rigid, high-strength, weight-bearing cast.

U.S. Pat. No. 4,376,438 (Straube et al.) discloses an orthopedic casting material wherein the tertiary amine catalyst is incorporated into the backbone of the polymer portion of the isocyanate-functional prepolymer. No separate catalyst is required.

U.S. Pat. No. 4,502,479 (Garwood et al.) discloses the use of tertiary alkanolamines, e.g., dimethylethanolamine, as catalysts in the curing of a water-curable isocyanate-functional prepolymer. At concentrations which do not adversely affect shelf stability, these catalysts do not cure as fast as desired by many experienced cast appliers.

U.S. Pat. No. 4,433,680 (Yoon) discloses the use of 2,2'-dimorpholinyldiethyl ether (DMDEE) as a catalyst in the cure of a water-curable isocyanate-functional prepolymer on an open-weave fibrous substrate to form an orthopedic bandage.

U.S. Pat. No. 4,705,840 (Buckanin) discloses the use of 2,2'-dimorpholinyldialkyl ethers substituted on one of the carbon atoms alpha to the central ether oxygen atom as catalysts in the curing of water-curable isocyanate-functional prepolymers.

Various compounds of Formula I below are known. For example, 2-(dialkylamino)ethyl 1-alkylprolinates are described in West German Pat. No. DE 1,933,411 (Likhosherstov et al., abstracted at Chemical Abstracts 76:153583m), *Khim.-Farm.Zh.* 1967, 1, 26 (Lebedeva et al., abstracted at Chemical Abstracts 67:82022d), and *Khim.-Farm.Zh.* 1973, 7, 10 (Likhosherstov et al., abstracted at Chemical Abstracts 79:53122d) as low toxicity ganglioplegic agents. Similarly, 2-(dialkylamino)ethyl 1-methylpipecolinates are described in Soviet Union Pat. No. 278027 (Likhosherstov et al., abstracted at Chemical Abstracts 74:53512c) as pharmaceutical agents. 2-(1-Piperidinyl)ethyl and 2-(4-morpholinyl)ethyl 4-morpholineacetates and 1-piperidineacetates are described in *Acta. Pol. Pharm.* 1979, 36 1 (Wolinski et al., abstracted at Chemical abstracts 91:123691n) as anticholinergic agents, and various aminoalkyl esters of piperidino- and morpholino- acetic acid are described in *Acta. Pol. Pharm.* 1980, 37, 397 (Wolinski et al., abstracted at Chemical Abstracts 95:80069d) and *Pol. J Pharmacol. Pharm.* 1978, 30, 497 (Faff et al., abstracted at Chemical Abstracts 91:32648n). 2-(Diethylamino)ethyl dimethylaminoacetate is described in *Farm.Zh.* (Kiev) 1990, 1, 38 (Grinevich et al., abstracted at Chemical Abstracts 114:42025q) as having significant inotropic activity. Also, 2-(diethylamino)ethyl N,N-dimethylglycinate is described in *Khim.-Farm.Zh.* 1983, 17, 916 (Razina et al., abstracted at Chemical Abstracts 99:169415u) and said to possess analgesic activity.

SUMMARY OF THE INVENTION

This invention provides curable compositions comprising an isocyanate-functional prepolymer and a catalytically effective amount of a compound of Formula I

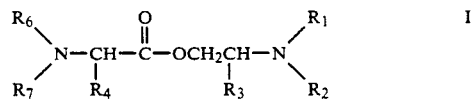

wherein:

$R_1$ and $R_2$ are independently straight chain, branched chain, or cyclic alkyl of one to about six carbon atoms, or $R_1$ and $R_2$ together form a straight chain or branched chain alkylene group having four or five carbons in the main alkylene chain, or $R_1$ and $R_2$ together form a group of the formula —A—O—B— or

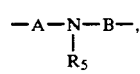

wherein A and B are independently straight chain or branched chain alkylene groups each having two carbon atoms in their main alkylene chain and $R_5$ is alkyl, aryl, or a deactivating substituent;

$R_3$ is hydrogen or straight chain, branched chain, or cyclic alkyl of one to about six carbon atoms, or $R_1$ and $R_3$ together form a straight chain or branched chain alkylene group having three or four carbon atoms in the main alkylene chain, with the proviso that when $R_1$ and $R_3$ together form a straight chain or branched chain alkylene group having three or four carbon atoms in the main alkylene chain, then $R_2$ is straight chain, branched chain, or cyclic alkyl of one to about six carbon atoms; $R_4$ is hydrogen, straight chain, branched chain, or cyclic alkyl of one to about six carbon atoms, $R_6$ and $R_7$ are independently straight chain, branched chain, or cyclic alkyl of one to about six carbon atoms, or $R_6$ and $R_7$ together form a straight chain or branched chain alkylene or alkenylene group with five carbons in the main alkylene or alkenylene chain, or $R_6$ and $R_7$ together form a group of the formula —A—O—B— or

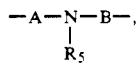

wherein A, B, and $R_5$ are as defined hereinabove, or $R_4$ and $R_6$ together form a straight chain or branched chain alkylene group having three or four carbon atoms in the main alkylene chain, with the proviso that when $R_4$ and $R_6$ together form a straight chain or branched chain alkylene group having three or four carbon atoms in the main alkylene chain, then $R_7$ is straight chain, branched chain, or cyclic alkyl of one to about six carbon atoms.

In addition, this invention provides casting articles comprising a flexible sheet with a coating of the above-described curable composition thereon.

This invention also provides a catalyzes method for catalyzing the cure of a water-curable isocyanate-functional prepolymer comprising forming a mixture of:
 a) an isocyanate-functional material,
 b) water, and
 c) a catalytically effective amount of a compound of Formula I.

Also, this invention provides methods of orthopedic casting using the above-described casting articles.

The use of the compounds of Formula I as catalysts affords water-curable compositions having good set times, satisfactory shelf stability and, when curing is initiated, affords materials having surprisingly good early strengths when compared to compositions comprising commonly used catalysts of the prior art. The compositions of the invention are useful as adhesives, foams, coatings, and sealants, and as the curable component of an orthopedic bandage.

DETAILED DESCRIPTION OF THE INVENTION

The compounds suitable for use as catalysts in this invention are compounds of Formula I above. $R_1$ and $R_2$ can be independently straight chain, branched chain, or cyclic alkyl of one to about six carbon atoms. $R_3$ can be hydrogen or straight chain, branched chain, or cyclic alkyl of one to about six carbon atoms. Alternatively, $R_1$ and $R_2$ along with the catenary nitrogen therebetween can form a pyrrolidine ring or a piperidine ring.

When $R_1$ and $R_2$ together form a group of the formula —A—O—B— or

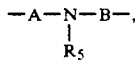

a morpholine ring or an N'-substituted piperazine ring for example can be formed. The N'-substituent $R_5$ is preferably a deactivating substituent, i.e., a group that substantially reduces the basicity of the N' nitrogen. For example alkylcarbonyl, arylcarbonyl, alkoxycarbonyl [—C(O)Oalkyl], dialkylaminocarbonyl [—C(O)N(alkyl)$_2$], alkylaminocarbonyl, arylaminocarbonyl, alkylarylaminocarbonyl, and the like are suitable and others can be easily selected by those skilled in the art. $R_5$ can also be an aryl group such as phenyl, naphthyl, or the like, including substituted aryl such as methylphenyl (i.e., tolyl) or methylnaphthyl. When $R_5$ is alkyl the number of carbon atoms in the alkyl group is not unduly critical to the utility of the compound as a catalyst.

As a further alternative, $R_1$ and $R_3$ together can form a straight chain or branched chain alkylene chain having three or four carbons in the main alkylene chain, i.e., $R_1$ and $R_3$ along with the catenary nitrogen and the methine carbon therebetween can form a pyrrolidine or piperidine ring. In an instance wherein $R_1$ and $R_3$ form a pyrrolidine or piperidine ring, $R_2$ is straight chain, branched chain, or cyclic alkyl of one to about six carbon atoms (i.e., the ring is an N-alkyl pyrrolidine or piperidine ring). $R_4$ and $R_6$ can optionally form a piperidine ring, in which case $R_7$ is straight chain, branched chain, or cyclic alkyl of one to about six carbon atoms (i.e., the compound is an ester of an N-alkyl-2-piperidine carboxylic acid, sometimes referred to as a 1-alkyl-pipecolinate). $R_4$ and $R_6$ can also optionally form a pyrrolidine ring in which case also $R_7$ is straight chain, branched chain, or cyclic alkyl of one to about six carbon atoms (i.e., the compound is an ester of an N-alkyl proline).

Preferred compounds of Formula I include: 2-(N,N-dimethylamino)ethyl 1-methylpipecolinate; 2-(1-methylpiperidyl)methyl 1-methylpipecolinate; 2-(1-piperidino)ethyl 1-piperidinoacetate; 2-(1-methylpiperidyl)methyl N,N-dimethylaminoacetate; 2-(1-morpholino)ethyl N,N-diethylaminoacetate; 2-(1-morpholino)ethyl alpha-(N-morpholino)propionate; 2-(N,N-dimethylamino)ethyl N,N-dimethylaminoacetate; and 2-(1-piperidino)ethyl N,N-dimethylaminoacetate; and 2-(1pyrrolidino)ethyl 1-methylpipecolinate. Most preferred are 2-(1-methylpiperidyl)methyl 1-methylpipecolinate and 2-(1-pyrrolidino)ethyl 1-methylpipecolinate.

These compounds are preferred because, when combined with an isocyanate-functional prepolymer, they provide resins with superior strength soon after curing is initiated when compared with the commonly used catalysts of the prior art.

Compounds useful in this invention contain a nitrogen both in the alcohol residue of the ester and in the acid residue of the ester. They can be prepared by the transesterification reaction shown below, wherein the alkoxy portion of an ester of Formula II is replaced by the alkoxy portion of a compound of Formula III:

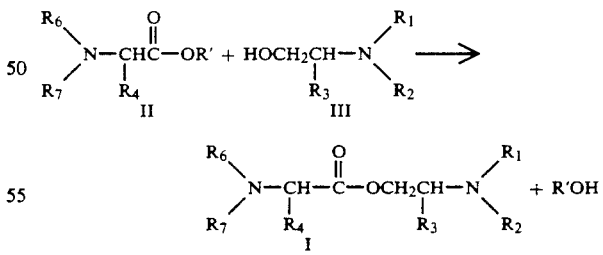

and wherein $R_1$, $R_2$, $R_3$, $R_4$, $R_6$ and $R_7$ are as defined above, and "—OR'" designates an alkoxy, phenoxy, or other group capable of being displaced during the transesterification reaction.

The transesterification reaction can be carried out under conventional conditions, e.g., conditions involving such catalysts as dibutyl tin oxide, titanium isopropoxide, alkali metals, alkali metal hydrides and the like. Preferably the catalyst is sodium or potassium or the hydrides of these metals, because the residues of these catalysts are readily neutralized and separated from the product. Tin catalysts are less preferred, because the presence of tin compounds in an isocyanate-functional material can decrease the shelf stability of the material by catalyzing undesirable side reactions such as allophanate formation.

Many synthetic intermediates of Formulas II and III are known. Others can be readily prepared from other known compounds by methods well known to those skilled in the art. Some compounds of Formula II, for example, are alkyl esters of either alpha-(N,N-dialkylamino)acetic acids or 1-cylic amine substituted acetic acids. Such compounds can be prepared from alkyl α-haloalkanoates (wherein halo is bromo or chloro) by reaction with suitable secondary amines. 2-carboxy-N-heterocyclics of Formula II can be prepared, e.g., by catalytic reduction of pyridine-2-carboxylic acids followed by methylation, or by catalytic reduction of an N-methyl quaternary salt of a 2-carboxypyridine.

Compounds of Formula III are 2-(N,N-disubstituted amino)alkyl alcohols. These compounds are also generally known and can be prepared, for example, from the corresponding secondary amine and a suitable epoxide by methods well known to those skilled in the art.

Compounds of Formula I are useful as catalysts for curing any isocyanate-functional material or composition. They are particularly useful for curing water-curable isocyanate-functional prepolymers. In this regard it is notable that the catalysts of the invention comprise an ester group and therefore would be expected to be relatively easily hydrolysed. Nonetheless, they function surprisingly well as catalysts of a reaction involving water.

Preferred prepolymers for use with the compounds of Formula I are based on aromatic isocyanates. Such prepolymers are generally prepared by reacting a polyol with an excess of a polyisocyanate under conventional conditions. Such prepolymers are well known to those skilled in the art and are disclosed, e.g., in U.S. Pat. Nos. 4,411,262 (von Bonin et al.), 4,433,680 (Yoon), 4,502,479 (Garwood et al.), 4,667,661 (Scholz et al.), 4,705,840 (Buckanin), and 4,758,648 (Rizk et al.), the disclosures of each being incorporated herein by reference. A suitable prepolymer for use in the curable compositions of the invention uses an isocyanate known as ISONATE TM 2143L isocyanate (a mixture containing about 73% of diphenylmethane-4,4'-diisocyanate, Dow) and a polypropylene oxide polyol known as NIAX TM Polyol PPG 725 (AC West Virginia Polyol Co.). To prolong the shelf-life of the material, it is preferred to include about 0.02-0.5 percent by weight of benzoyl chloride or other suitable stabilizer. The most preferred curable compositions, casting articles, catalyzes methods, and orthopedic casting methods of the invention involve prepolymers described in co-pending, commonly assigned U.S. patent application Ser. No. 07/376,421, filed Jul. 7, 1989, entitled "Curable Resins With Reduced Foaming Characteristics And Articles Incorporating Same", the disclosure of which is incorporated herein by reference.

The curable compositions of the invention comprise an isocyanate-functional material and a catalytically effective amount of a compound of Formula I. As used herein, the term "an effective amount" designates an amount of a component sufficient to provide the desired physical properties (e.g., cure rate, layer to layer lamination, and strength) to the curable composition. The particular amount of compound that constitutes a catalytically effective amount will vary with the particular compound used, the particular isocyanate-functional material used, the particular applications of the curable composition, and the set time that is desired for the curable composition. Particular amounts are easily selected by those skilled in the art and are set forth generally below with respect to particular applications.

In order to prepare a curable composition of the invention, an isocyanate-functional material and a compound of Formula I can be mixed using conventional mixing techniques. In order to avoid premature curing of the resulting curable composition, the mixing should be done under anhydrous conditions, preferably in a substantially inert atmosphere, e.g., nitrogen gas. The resulting curable composition should also be stored under anhydrous conditions in a container substantially impermeable to oxygen and water vapor.

The curable compositions of the invention can be cured by exposure to water, e.g., water vapor or liquid water. For sealants, adhesives, and coatings, ordinary ambient humidity is usually adequate to promote cure. Heat or high humidity will accelerate cure, and low temperatures (e.g., 5° C. or less) or low humidity (e.g., 15% relative humidity or less) will retard cure. Bonds to damp substrates (e.g., wood) typically cure faster than bonds to dry substrates (e.g., glass). The reactivity of a curable composition once it is exposed to water as a curing agent can be controlled by the amount of the compound of Formula I present in the curable composition. A catalytically effective amount of the compound of Formula I is the amount necessary to achieve the desired reactivity.

One of the most advantageous uses of the curable compositions of this invention is in orthopedic casting applications, where the composition is used as the resin component of a resin-coated flexible sheet, which resin component hardens on exposure to water. (As used herein, the term "coating" is intended to designate not only a surface application of composition, but also an application wherein a sheet material is impregnated with a composition, i.e., wherein the composition surrounds the fibers of the sheet material, or wherein the composition is absorbed by the fibers).

For use in orthopedic casting, the reactivity of the curable composition must not be so great that: (1) a hard film quickly forms on the surface of the composition preventing further penetration of the water into the bulk of the composition; or (2) the cast becomes rigid before the application and shaping is complete. The particular preferred amount of compound of Formula I will depend upon the nature of the isocyanate-functional material, the desired set time, and the curing conditions. When the material is an isocyanate-functional polyurethane prepolymer based on an aromatic isocyanate, the amount of compound of Formula I suitable for orthopedic casting applications will generally range from about 0.1% to about 5% by weight of the isocyanate-functional prepolymer, preferably from about 0.1 to about 3%, most preferably from about 0.2 to about 2%.

Foaming of the composition is preferably minimized because foaming reduces the porosity of the cast and its overall strength. Foaming occurs because carbon dioxide is released when water reacts with isocyanate groups. One way to minimize foaming is to add a foam suppresser such as ANTIFOAM TM A silicone fluid (Dow Corning), ANTIFOAM TM 1400 silicone fluid (Dow Corning), or L550 or L5303 silicone surfactants.

It is preferred to use a silicone liquid such as Dow Corning ANTIFOAM TM 1400 silicone fluid at a concentration of about 0.1 to 1.0 percent by weight.

The casting articles of this invention, useful as orthopedic casting tapes, comprise a flexible sheet material with a water-curable composition coated thereon. They are preferably prepared by forming an isocyanate-functional prepolymer in the presence of a compound of Formula I as described above and coating the resulting curable composition onto a flexible sheet material, e.g., a fabric.

In the preferred embodiments relating to casting articles, a porous, flexible sheet material is used. The porous material is preferably impregnated with the composition. A preferred example of a porous, flexible sheet material that can be impregnated with the composition of this invention is disclosed in U.S. Pat. No. 4,502,479. The sheet material disclosed therein imparts high structural strength to an orthopedic bandage prepared therefrom. A particularly preferred sheet material for use in the casting articles of this invention is the scrim used as the scrim component of SCOTCHCAST TM 2 Casting Tape (3M), described in U.S. Pat. No. 4,609,578, Example 1. The sheet material is a fiberglass fabric comprised of extensible knit fiberglass that exhibits an extensibility of at least about 20% in the length direction and has been heat set without tension in order to reduce fraying.

The amount of composition applied to the sheet material for use as a casting article such as an orthopedic casting tape must be sufficient for formation of a strong interlayer laminate bond but not so great as to occlude the porosity and unnecessarily thicken the sheet, which should be thin for rapid and complete hardening. Excessive composition can also cause the casting article to be messy to handle because of stickiness or dripping and transfer of composition.

The sheet material used in a casting article (e.g., an orthopedic casting tape) is generally formed in rolls of various widths, generally from 2.5 cm (one inch) to about 15 cm (six inches) wide. The sheet material can be coated with the curable composition in an amount, in terms of weight, of about 50 to about 500 g/m$^2$. In a preferred embodiment using a fiberglass fabric the curable composition preferably constitutes about 35% to about 50% by weight of the coated casting article. Generally, the composition will flow into the capillary spaces between contiguous filaments of the sheet material and will become rigidly bonded upon curing.

A casting article (e.g., an orthopedic casting tape) can be in the form of a roll wound up on a plastic core or in the form of a rolled or folded multi-layer laminate splint. The article can be sealed within a moisture- and oxygen-impermeable container such as an aluminum foil pouch. For use, the container is opened and the article is fully immersed and squeezed in tap water for about 5 to 30 seconds to replace entrapped air with water. Generally a sufficient amount of water is absorbed by the article in this manner. When a roll is unwound during wrapping of a cast, the excess moisture coats the freshly exposed composition surfaces insuring thorough wetting and rapid hardening. An alternate but less preferable method involves wrapping the cast without dipping and then allowing atmospheric moisture or water provided by spraying or by application of a wet towel to cure the composition.

Prior to applying an orthopedic cast to a limb or body member of a patient, a protective layer can be positioned about the limb or body member. The protective layer can take the form of a tubular stockinet or some other convenient form such as, for example, an elongate, non-woven, cotton, or polyester strip or bandage that can be wrapped about the limb or body member.

With the protective layer in a proper position, the moistened casting article can be wrapped about the body member and over the protective layer in a manner similar to that used in applying an elastic-type bandage. The cast can be shaped in a manner similar to that used in shaping a plaster-of-paris cast.

Eight or fewer layers of the cast material are generally sufficient to form a cast having significant strength within 8 minutes and having weight-bearing strength within 30 minutes. A fully cured cylindrical laminate having eight or fewer layers, e.g., six layers, should support at least about 3.6 kg/cm (20 lb/inch) and preferably at least about 7.2 kg/cm (40 lb/inch) of cylinder length according to the dry strength ring strength test described in detail below.

Ring Strength Test

In this test, the "dry strength" of cured cylinders of resin-coated materials is determined. For this test, cured cylinders are formed as described below so as to form six-layered cylinders around a 2 inch (5.08 cm) mandrel.

Each cylinder ring is formed by removing a roll of 3 inch (7.62 cm) wide resin-coated material from its storage pouch and immersing the roll completely in deionized water having a temperature of about 80° F. (27° C.) for about 30 seconds. The roll of resin-coated material is then removed from the water and the material is wrapped around a 2 inch (5.08 cm) mandrel covered with a thin stockinet to form six complete uniform layers using a controlled wrapping tension of about 45 grams per centimeter width of the material. Each cylinder is completely wound within 30 seconds after removal of the roll from the water.

Thirty minutes after initial immersion in water, each cylinder is removed from its respective mandrel and allowed to cure for 48–60 hours in a controlled atmosphere of 75° F.±3° F. (34°±2° C.) and 55%±5% relative humidity. Each cylinder is then placed in the fixture of an INSTRON TM tensile testing machine. Compression loads are applied to the cylinder along its exterior and parallel to its axis. The cylinder is placed lengthwise between the two bottom bars of the fixture (the bars being 1.9 centimeters wide, 1.3 centimeters in height, and 15.2 centimeters long, and spaced about 4 centimeters apart). The inside edges Of the bars have a curbed surface having a ⅛ inch (0.3 cm) radius. A third bar (0.63 cm wide, 2.5 cm high, and 15.2 cm long) is then centered over the top of the cylinder, parallel to its axis. The contacting (bottom) edge of the third bar has a curved surface having a ⅛ inch (0.31 cm) radius. The third bar is brought down to bear against and crush the cylinder at a speed of about 5 cm/min. The maximum or peak force applied while crushing the cylinder is recorded as the ring strength, which in this particular instance is the "dry strength" (expressed in terms of force per unit length of the cylinder, i.e., newtons/cm). For each material, at least five samples are tested, and the average peak force applied is calculated and reported as the "dry strength".

In addition to the above-described use in orthopedic casting, curable compositions of this invention will be useful in a variety of applications wherein isocyanate-functional materials have been used previously, e.g., as sealants (e.g., caulks), coatings, foams, adhesives, and so forth. They can be applied to a variety of articles and substrates, such as articles or substrates of glass, metal, plastic, wood, leather, masonry, textiles, and the like.

When used as an adhesive, the composition is placed between an article and a substrate, in contact with both, and exposed to moisture sufficient to cure the composition. When used as a coating, the composition is deposited as a continuous layer on the surface of the article to be coated and exposed to moisture sufficient to cure the composition. When used as a sealant, the composition is deposited in the void to be sealed and exposed to moisture sufficient to cure the composition. When used as a structural reinforcing material, the composition is coated onto and/or impregnated into an article comprised of a flexible sheet of fibrous or nonfibrous fabrics, papers, felts, foams and the like and exposed to moisture sufficient to cure the composition. When used for making foams the compositions are usually mixed with a precise amount of water and immediately packed into an appropriate mold. For such applications wherein the isocyanate-functional material is an isocyanate-functional polyurethane prepolymer based on an aromatic isocyanate, an effective amount of compound of Formula I preferably is about 0.002 to 2 weight percent, and most preferably about 0.05 to 0.5 weight percent based upon the weight of prepolymer.

Other ingredients and adjuvants can be incorporated into the compositions of the invention. Suitable ingredients and adjuvants and effective amounts thereof are disclosed, e.g. in U.S. Pat. No. 4,705,840 (Buckanin) and are easily selected by those skilled in the art.

The compositions of the invention can be put into packages according to techniques known to those skilled in the art. Suitable packages include, for example, aluminum foil laminate pouches, caulking tubes (made, for example, of aluminum foil laminates, metal or plastic), screw-capped squeezable tubes, cans, drums, and the like.

Several compounds of Formula I were prepared as follows:

CATALYST A 2-(N,N-Dimethylamino)ethyl N,N-Dimethylaminoacetate

A mixture of 65.5 g (0.5 mol) of ethyl N,N-dimethylglycinate, 44.6 g (0.5 mol) of N,N-dimethylethanolamine and 0.82 g of dibutyltin oxide was heated at about 130° C. The ethanol by-product was collected in a Dean-Stark trap. When the rate of ethanol evolution and amount of ethanol collected showed that the reaction was essentially complete, the reaction was heated at about 180° C. until ethanol evolution ceased. The liquid product was purified by distillation at reduced pressure to provide 2-(N,N-dimethylamino)ethyl N,N-dimethylaminoacetate.

CATALYST B 2-(1-Piperidino)ethyl N,N-Dimethylaminoacetate

Using the method of Example 1, 65.6 g ethyl N,N-dimethylglycinate was reacted with 64.6 g of 2-(1-piperidino)ethanol and 0.97 g of dibutyltin oxide to provide the desired product, which was purified by distillation.

CATALYST C 2-(N,N-Dimethylamino)ethyl N-methylpipecolinate

A mixture of 85 g (0.5 mol) of ethyl 1-methylpipecolinate, 44.6 g (0.5 mol) of N,N-dimethylethanolamine and 0.82 g of dibutyltin oxide was heated at about 145° C. for 30 hours. The ethanol by-product was collected in a Dean-Stark trap. When the rate of ethanol evolution and amount of ethanol collected showed that the reaction was essentially complete, the reaction was heated at about 180° C. until ethanol evolution ceased. The liquid product was purified by distillation at reduced pressure to provide 2-(N,N-dimethylamino)ethyl N-methylpipecolinate.

CATALYST D

N-Methyl-(2-piperidyl)methyl N-Methylpipecolinate

A mixture of 85.6 g (0.5 mole) of ethyl 1-methylpipecolinate, 64.6 g (0.5 mole) of 1-methyl-2piperidinemethanol and 1.1 g dibutyltin oxide was heated at 130° C. for three hours and then gradually heated to 200° C. When the amount of ethanol collected indicated the reaction was essentially complete the liquid product, N-methyl-(2-piperidyl)methyl N-methylpipecolinate, was distilled at 0.25 mm Hg pressure at about 130° C. The nuclear magnetic resonance and infrared spectra of the product were consistent with the structural assignment.

CATALYST E

N-Methyl-(2-piperidyl)methyl N,N-Dimethylaminoacetate

A mixture of 75 g of ethyl N,N-dimethylglycinate, 75 g of 1-methyl-2-piperidylmethanol and 1 g of titanium tetra(n-butoxide) was heated at 45° C. until the amount of ethanol collected indicated the reaction was complete. After cooling a small amount of water was added, the mixture was filtered, and the filtrate was distilled under reduced pressure to provide N-methyl-2-piperidylmethyl N,N-dimethylaminoacetate.

CATALYST F 2-(N-Morpholino)ethyl 2-(N-Morpholino)-propionate

To 174 g of morpholine was added slowly with stirring 181 g of ethyl 2-bromopropionate. To the stirred mixture was added 200 ml of diethyl ether while maintaining the temperature about 35° C. After about 16 hours 700 ml of toluene was added, then the insoluble salts were removed by filtration. The salts were neutralized by the addition of potassium carbonate, then extracted with toluene. The toluene filtrate and extracts were evaporated to provide 158 g of ethyl 2-(N-morpholino)propionate.

To 50 g of ethyl 2-(N-morpholino)propionate was added 50 g of N-(2-hydroxyethyl)morpholine and 0.5 g of dibutyltin oxide. This mixture was heated to 150° C. A Dean Stark trap was used to collect evolved ethanol. After 2 hours the temperature was elevated to 75° C. and maintained at that temperature for 3 hours. After a total of 14 ml of ethanol had been collected, the product was purified by vacuum distillation to provide 2-(N-morpholino)ethyl 2-(N-morpholino)propionate as a crystalline solid.

CATALYST G

2-(N-Morpholino)ethyl N,N-Diethylaminoacetate

To a mixture of 70 g of N-[(2-hydroxy)ethyl]-morpholine and 85 g of ethyl (N,N-diethylamino)acetate was added 0.8 g of dibutyltin oxide and the mixture was heated to 145° C. A Dean Stark trap was used to collect the evolved ethanol. An additional 0.4 g of dibutyltin oxide was added and the temperature was increased gradually to 180° C. over several hours. The total volume of ethanol collected was 28 ml. The product, 2-(N-morpholino)ethyl N,N-diethylaminoacetate, was separated by vacuum distillation. The structural assignment was confirmed by nuclear magnetic resonance and infrared spectral analysis.

CATALYST H

2-(N-Morpholino)ethyl N,N-Dimethylaminoacetate

Using the general method used to prepare Catalyst G but using ethyl (N,N-dimethylamino)acetate, the product 2-(N-morpholino)ethyl N,N-dimethylaminoacetate was obtained by vacuum distillation.

CATALYST I

2-(1-Pyrrolidino)ethyl 1-Methylpipecolinate

Using the general method used to prepare Catalyst G but using N-(2-hydroxyethyl)pyrrolidine and ethyl 1-methylpipecolinate the product 2-(1-pyrrolidino)ethyl 1-methylpipecolinate was obtained by vacuum distillation.

CATALYST J

2-(1-Pyrrolidino)ethyl N,N-Dimethylaminoacetate

Using the general method used to prepare Catalyst G but using N-(2-hydroxyethyl)pyrrolidine and ethyl N,N-dimethylaminoacetate the product 2-(1-pyrrolidino)ethyl N,N-dimethylaminoacetate was obtained by vacuum distillation.

pKa

Several catalysts were characterized by their titration curves (i.e., their pKa values) as follows:

To a 0.1 g sample of a catalyst was added with stirring 60 ml of distilled water, then 10 ml of 0.1N hydrochloric acid was added. The solution was stirred for 10 minutes, then backtitrated with 0.1N sodium hydroxide solution. The pH during backtitration was measured potentiometrically using a Metrohm Model 670 TITROPROCESSOR TM potentiometer (Brinkman Instruments Inc., Westbury, N.Y.). The endpoint and half-neutralization point were determined by the instrument, and for the purposes of this determination the half-neutralization point is taken as the pKa. The values of pKa for several catalysts are shown in Table I below.

TABLE I

| Catalyst | Measured pKa | |
|---|---|---|
| | First | Second |
| NCH₂C(O)OCH₂CH₂N (piperidine-piperidine) | 8.97 | 6.72 |
| (CH₃)₂NCH₂C(O)OCH₂CH₂N(CH₃)₂ | 8.53 | 6.49 |
| (CH₃CH₂)₂NCH₂C(O)OCH₂CH₂N(morpholine) | 7.56 | 5.36 |
| CH₃-N(piperidine)-C(O)OCH₂-N(piperidine)-CH₃ | 8.85 | 6.41 |
| (CH₃)₂NCH₂C(O)OCH₂-N(piperidine)-CH₃ | 9.05 | 6.4 |

The following Examples are provided to illustrate the invention and are not intended to limit the scope of the invention. Parts and percentages are by weight unless otherwise indicated, and temperatures are designated in degrees Celsius.

EXAMPLES 1-9

Compositions of the invention useful, for example, in connection with orthopedic casting materials, sealants, adhesives, foams, or coatings, were prepared and their gel times were measured as set forth below:

To a stirred 30.00 g sample of ISONATE TM 2143L isocyanate (Dow) in a 100 mL (4.5 cm diameter) polyethylene beaker was added 0.30 g of a selected catalyst, then 10 ml of water was added gently from a syringe. The mixture was stirred by hand with a 1.7 cm wide wooden tongue depressor at a rate of about 60 to 75 rpm. This time until gelation occurred was recorded. Gelation was defined as the point at which the viscosity was sufficient to allow formation of a permanent depression in the mixture.

Results are shown in Table II below.

TABLE II

| Catalyst | Example | Gel Time (Sec.) |
|---|---|---|
| (CH₃)₂NCH₂C(O)OCH₂CH₂N(pyrrolidine) | 1 | 28 |
| (piperidine)NCH₂C(O)OCH₂CH₂N(piperidine) | 2 | 85 |
| (CH₃)₂NCH₂C(O)OCH₂CH₂N(CH₃)₂ | 3 | 71 |
| (CH₃)₂NCH₂C(O)OCH₂CH₂N(piperidine) | 4 | 120 |
| (CH₃)₂NCH(CH₃)C(O)OCH₂CH₂N(morpholine) | 5 | 184 |

TABLE II-continued

| Catalyst | Example | Gel Time (Sec.) |
|---|---|---|
| (CH$_3$)$_2$NCH$_2$C(O)OCH$_2$CH$_2$N⟨piperidine ring with O⟩ | 6 | 213 |
| piperidyl-CH(CH$_3$)-C(O)OCH$_2$-piperidyl(CH$_3$) | 7 | 35 |
| piperidyl(CH$_3$)-C(O)OCH$_2$CH$_2$N(CH$_3$)$_2$ | 8 | 71 |
| (CH$_3$)$_2$NCH$_2$C(O)OCH$_2$-piperidyl(CH$_3$) | 9 | 38 |

EXAMPLE 10

A curable composition of the invention useful, for example, in connection with an orthopedic casting material, a sealant, an adhesive, a foam, or a coating, was prepared as follows:

An amount, 1125 g (7.76 equivalents), of ISONATE TM 2143L isocyanate (modified diphenylmethane diisocyanate, Dow) was added to a one gallon (4L) jar having a three-necked lid equipped with a thermometer, stirrer and nitrogen inlet. To this was added 30.0 g (about 1.5 weight percent) of 2-(1-piperidino)ethyl N,N-dimethylaminoacetate (Catalyst B), 1.0 g of paratoluenesulfonyl chloride, 80 g of PLURONIC TM F-108 polyethylene oxide-polypropylene oxide block copolymer (available from BASF Wyandotte Corporation), and 3.6 g of Dow-Corning DB-100 silicone fluid. This was followed by the addition of 9.6 g of BHT (2,6-di-tert-butyl-4-methylphenol) in 480 g of NIAX TM PPG-725 (a polypropylene oxide polyol having a molecular weight of about 750, AC West Virginia Polyol Co.) and 270 g of NIAX TM PPG-425 (a polypropylene oxide polyol having a molecular weight of about 425, AC West Virginia Polyol Co.). The theoretical equivalent ratio of isocyanato groups to hydroxyl groups was 3.15:1 and the isocyanato equivalent weight of the resulting prepolymer was 375 g/equivalent. The addition of the polyol mixture was made through a dropping funnel over a period of thirty minutes. After addition the polymerization reaction was carried out at 50°-60° C. for one hour to afford a curable composition of the invention.

EXAMPLE 11

Using the general method of Example 10, 2-(N,N-dimethylamino)ethyl N,N-dimethylaminoacetate (Catalyst A) was incorporated (in an amount of about 1.0 percent by weight) into a curable composition of the invention.

EXAMPLES 12–15 AND COMPARATIVE EXAMPLES C-1 AND C-2

As shown in Table III below, curable compositions of the invention useful, for example, in connection with orthopedic casting materials, sealants, adhesives, foams, or coatings, and comparative compositions were prepared in the general manner described in Example 10. While still hot (49°–60° C.) the compositions were poured into 240 mL (8 oz) jars and the jars were sealed. The samples were subjected to accelerated aging conditions of 49° C. in the sealed glass jars. Individual samples were periodically cooled to room temperature and then equilibrated for at least 4 hours in a water bath at 23° C. The viscosity of the cooled sample was measured using a SYNCHROLECTRIC TM Viscometer Model RVT (Brookfield Engineering Labs, Inc., Spoughton, Mass.) using spindles #6 and #7. Viscosity values are set forth in Table III below.

TABLE III

| | Example | | | | | |
|---|---|---|---|---|---|---|
| | 12 | 13 | 14 | 15 | C-1 | C-2 |
| | Catalyst (concentration in weight percent) | | | | | |
| Day | D (0.5%) | H (3.8%) | A (1.0%) | * (1.75%) | ** (1.32%) | *** (0.5%) |
| | Viscosity (cps × 10$^{-3}$) | | | | | |
| 0 | 77 | 64 | 70.5 | 63.5 | 65 | 67 |
| 4 | 57 | 52 | 53.5 | 55 | 50 | 138 |
| 10 | 64.5 | 60 | 69.5 | 69.5 | 62 | 830 |
| 15 | 83 | 67 | 93 | 87 | 69 | >2000 |
| 20 | 86 | 73 | 94 | 92.5 | 73 | NT |
| 28 | 102 | 86 | 124 | 112 | 82 | NT |
| 33 | 128 | 102 | 164 | 156 | 98 | NT |
| 38 | 140 | 126 | 184 | 196 | 112 | NT |
| 43 | 136 | NT | 202 | 194 | 96 | NT |
| 48 | 160 | NT | NT | 224 | 112 | NT |

NT = Not Taken
*2-(N-piperidyl)ethyl N-piperidyl acetate
**morpholinoethyl morpholinoisopropyl ether
***[(CH$_3$)$_2$NCH$_2$CH$_2$]$_2$O The results in Table III show that these compositions of the invention age well compared to Comparative Example C-2.

EXAMPLES 16–17 AND COMPARATIVE EXAMPLES C-3 AND C-4

Curable compositions of the invention useful, for example, in connection with orthopedic casting materials, sealants, adhesives, foams, or coatings, and comparative compositions were prepared as described in general terms in Example 10 using various catalysts as shown in Table IV below. The amount of catalyst used was selected to provide a set time of about 3 minutes.

240 mL (8 oz) samples of the compositions of Examples 16 and 17 and Comparative Examples C-3 and C-4 were subjected to accelerated aging conditions of 49° C. in sealed glass jars. Individual samples were periodically cooled to room temperature and then equilibrated for 2 hours in a water bath at 23° C. The viscosity of the cooled sample was measured using a SYNCHRO-LECTRIC TM Viscometer Rodel RVT (Brookfield Engineering Labs, Inc., Spoughton, Mass.) using spindles #6 and #7. The viscosities are set forth in Table IV below.

TABLE IV

| | Example | | | |
|---|---|---|---|---|
| | 16 | 17 | C-3 | C-4 |
| | Catalyst | | | |
| | (concentration in weight percent) | | | |
| | E | B | | |
| Day | (0.5%) | (1.6%) | (2.3%)* | (1.32)** |
| | Viscosity (cps × 10) | | | |
| 0 | 75 | 53 | 62.5 | 48 |
| 7 | 84 | 66 | 74 | 52 |
| 12 | 94 | 78 | 86 | 64 |
| 17 | 108 | 92 | 108 | 68 |
| 28 | 104 | 92 | 86 | 66 |
| 35 | 114 | 102 | 98 | 71.5 |
| 42 | 130 | 126 | 108 | 74 |
| 49 | 155 | 166 | 164 | 96 |

*2,2'-Dimorpholinodiethyl ether
**Morpholinoethyl morpholinoisopropyl ether

The results in Table IV show that upon accelerated aging these casting articles of the invention exhibit viscosity increases comparable to those of the Comparative Examples.

What is claimed is:

1. A storage stable curable composition comprising (i) an isocyanate-functional material; and (ii) a catalytically effective amount of a compound of the formula

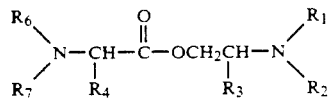

wherein $R_1$ and $R_2$ are independently straight chain, branched chain, or cyclic alkyl of one to about six carbon atoms, or $R_1$ and $R_2$ together form a straight chain or branched chain alkylene group having four or five carbons in the main alkylene chain, or $R_1$ and $R_2$ together form a group of the formula —A—O—B— or

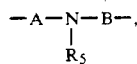

wherein A and B are independently straight chain or branched chain alkylene groups each having two carbon atoms in their main alkylene chain and $R_5$ is alkyl, aryl, or a deactivating substituent;

$R_3$ is hydrogen or straight chain, branched chain, or cyclic alkyl of one to about six carbon atoms, or $R_1$ and $R_3$ together form a straight chain or branched chain alkylene group having three or four carbon atoms in the main alkylene chain, with the proviso that when $R_1$ and $R_3$ together form a straight chain or branched chain alkylene group having three or four carbon atoms in the main alkylene chain, then $R_2$ is straight chain, branched chain, or cyclic alkyl of one to about six carbon atoms; $R_4$ is hydrogen, straight chain, branched chain, or cyclic alkyl of one to about six carbon atoms, $R_6$ and $R_7$ are independently straight chain, branched chain, or cyclic alkyl of one to about six carbon atoms, or $R_6$ and $R_7$ together form a straight chain or branched chain alkylene or alkenylene group with five carbons in the main alkylene or alkenylene chain, or $R_6$ and $R_7$ together form a group of the formula —A—O—B— or

wherein A, B and $R_5$ are as defined hereinabove, or $R_4$ and $R_6$ together form a straight chain or branched chain alkylene group having three or four carbon atoms in the main alkylene chain, with the proviso that when $R_4$ and $R_6$ together form a straight chain or branched chain alkylene group with three or four carbon atoms in the main alkylene chain then $R_7$ is straight chain, branched chain, or cyclic alkyl of one to about six carbon atoms.

2. A curable composition according to claim 1, wherein the isocyanate-functional material is an isocyanate-functional prepolymer based on an aromatic isocyanate.

3. A curable composition according to claim 1, wherein the compound is selected from the group consisting of: 2-(N,N-dimethylamino)ethyl 1-methylpipecolinate; 2-(1-methylpiperidyl)methyl 1-methylpipecolinate; 2-(1-piperidino)ethyl 1-piperidinoacetate; 2-(1methylpiperidyl)methyl N,N-dimethylaminoacetate; 2-(1-morpholino)ethyl N,N-diethylaminoacetate; 2-(1-morpholino)ethyl alpha-(N-morpholino)propionate; 2-(N,N-dimethylamino)ethyl N,N-dimethylaminoacetate; 2-(1pyrrolidino)ethyl 1-methylpipecolinate; and 2-(1piperidino)ethyl N,N-dimethylaminoacetate.

4. A catalyzes method for catalyzing the cure of an isocyanate-functional material comprising the steps of
  (i) forming a mixture of:
    a) an isocyanate-functional material, and
    b) a catalytically effective amount of a compound of the formula

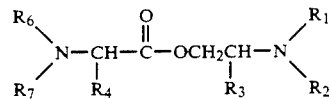

wherein $R_1$ and $R_2$ are independently straight chain, branched chain, or cyclic alkyl of one to about six carbon atoms, or $R_1$ and $R_2$ together form a straight chain or branched chain alkylene group having four or five carbons in the main alkylene chain, or $R_1$ and $R_2$ together form a group of the formula —A—O—B— or

wherein A and B are independently straight chain or branched chain alkylene groups each having two carbon atoms in their main alkylene chain and $R_5$ is alkyl, aryl, or a deactivating substituent;

$R_3$ is hydrogen or straight chain, branched chain, or cyclic alkyl of one to about six carbon atoms, or $R_1$ and $R_3$ together form a straight chain or branched chain alkylene group having three or four carbon atoms in the main alkylene chain, with the proviso that when $R_1$ and $R_3$ together form a straight chain or branched chain alkylene group having three or four carbon atoms in the main alkylene chain, then $R_2$ is straight chain, branched chain, or cyclic alkyl of one to about six carbon atoms;

$R_4$ is hydrogen, straight chain, branched chain, or cyclic alkyl of one to about six carbon atoms, $R_6$ and $R_7$ are independently straight chain, branched chain, or cyclic alkyl of one to about six carbon atoms, or $R_6$ and $R_7$ together form a straight chain or branched chain alkylene or alkenylene group with five carbons in the main alkylene or alkenylene chain, or $R_6$ and $R_7$ together form a group of the formula —A—O—B— or

wherein A, B and $R_5$ are as defined hereinabove, or $R_4$ and $R_6$ together form a straight chain or branched chain alkylene group having three or four carbon atoms in the main alkylene chain, with the proviso that when $R_4$ and $R_6$ together form a straight chain or branched chain alkylene group with three or four carbon atoms in the main alkylene chain then $R_7$ is straight chain, branched chain, or cyclic alkyl of one to about six carbon atoms, and, (ii) adding water to the mixture of step (i).

5. A method according to claim 4, wherein the isocyanate-functional material is an isocyanate-functional prepolymer based on an aromatic isocyanate.

6. A method according to claim 4, wherein the compound is selected from the group consisting of: 2-(N,N-dimethylamino) ethyl 1-methylpipecolinate; 2-(1-methylpiperidyl)methyl 1-methylpipecolinate; 2-(1-piperidino)ethyl 1-piperidinoacetate; 2-(1-methylpiperidyl)methyl N,N-dimethylaminoacetate; 2-(1-morpholino)ethyl N,N-diethylaminoacetate; 2-(1-morpholino)ethyl alpha-(N-morpholino propionate; 2-(N,N-dimethylamino)ethyl N,N-dimethylaminoacetate; 2-(1-pyrrolidino)ethyl 1-methylpipecolinate; and 2-(1-piperidino)ethyl N,N-dimethylaminoacetate.

7. An article comprising a flexible sheet material coated with a composition according to claim 1.

8. An article according to claim 7 in the form of an orthopedic casting tape.

9. A method of orthopedic casting comprising the steps of:
(i) providing a flexible sheet material coated with a composition according to claim 1;
(ii) contacting the coated sheet material with water in order to initiate cure of the composition; and
(iii) applying the coated sheet material to a body member of a subject.

* * * * *

UNITED STATES PATENT AND TRADEMARK OFFICE
CERTIFICATE OF CORRECTION

PATENT NO. : 5,225,513
DATED : July 6, 1993
INVENTOR(S) : Matthew T. Scholz, et. al.

It is certified that error appears in the above-indentified patent and that said Letters Patent is hereby corrected as shown below:

Title page, item [57], Abstract, first line, "Catalyzes" should be -- Catalysis --.

Col. 3, line 20, "catalyzes" should be -- catalysis --.
Col. 8, line 49, "Of" should be -- of --.
Col. 8, line 50, "0.3" should be -- 0.31 --.
Col. 10, line 38, "45°C" should be -- 145°C --.
Col. 10, line 62, "75°C" should be -- 175°C --.
Col. 15, line 8, "(cps x 10)" should be -- (cps x $10^{-3}$) --.
Col. 16, line 31, "catalyzes" should be -- catalysis --.

Signed and Sealed this

Thirtieth Day of August, 1994

Attest:

BRUCE LEHMAN

*Attesting Officer*     *Commissioner of Patents and Trademarks*